(12) United States Patent
Barenholz et al.

(10) Patent No.: US 7,985,417 B2
(45) Date of Patent: Jul. 26, 2011

(54) METHOD OF LIPID STRUCTURE PREPARATION

(75) Inventors: Yechezkel Barenholz, Jerusalem (IL); Olga Garbuzenko, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1412 days.

(21) Appl. No.: 11/246,340

(22) Filed: Oct. 7, 2005

(65) Prior Publication Data

US 2006/0121105 A1 Jun. 8, 2006

Related U.S. Application Data

(60) Provisional application No. 60/617,505, filed on Oct. 8, 2004.

(51) Int. Cl.
*A61K 9/127* (2006.01)
(52) U.S. Cl. .................................................. 424/450
(58) Field of Classification Search .................. None
See application file for complete search history.

(56) References Cited

U.S. PATENT DOCUMENTS

| | | | |
|---|---|---|---|
| 5,013,556 A | | 5/1991 | Woodle et al. |
| 5,393,530 A | * | 2/1995 | Schneider et al. ............ 424/450 |
| 5,395,619 A | | 3/1995 | Zalipsky et al. |
| 5,616,790 A | | 4/1997 | Arnold et al. |
| 5,631,018 A | | 5/1997 | Zalipsky et al. |
| 5,891,468 A | | 4/1999 | Martin et al. |
| 5,922,594 A | | 7/1999 | Löfås |
| 6,180,134 B1 | | 1/2001 | Zalipsky et al. |
| 6,214,388 B1 | | 4/2001 | Benz et al. |
| 6,316,024 B1 | * | 11/2001 | Allen et al. .................... 424/450 |
| 6,326,353 B1 | | 12/2001 | Zalipsky et al. |
| 6,479,034 B1 | | 11/2002 | Unger et al. |
| 2003/0031704 A1 | | 2/2003 | Huang et al. |

FOREIGN PATENT DOCUMENTS

| | | |
|---|---|---|
| WO | WO 98/23948 | 6/1998 |
| WO | WO 99/55367 | 11/1999 |
| WO | WO 01/26800 A1 | 4/2001 |

OTHER PUBLICATIONS

SA Galema. Microwave Chemistry. Chemical Society Reviews, 1997, vol. 26, pp. 233-238.*
I Ahmad, M Longenecker, J Samuel, TM Allen. "Antibody-Targeted Delivery of Doxorubicin Entrapped in Sterically Stabilized Liposomes Can Eradicate Lung Cancer in Mice." Cancer Research 53, Apr. 1, 1993, p. 1484-1488.*
Allen, T.M., et al., *Biochim. Biophys. Acta*, 1237:99-108, (1995).
Amselem, S., et al., *Journal of Pharmaceutical Science*, 79(12):1045-1052, (1990).
Blume, G., et al., *Biochimica et Biophysica Acta*, 1149:180-184, (1993).
Druckman, S., et al., *Biochimica et Biophysica Acta*, 980:381-384, (1989).
Groves, J.T. and Dustin, M.L., *Journal of Immunological Methods*, 278:19-32, (2003).
Hanke, W. and Schlue, W.R., Planar Lipid Bilayers, D.B. Sattelle Ed., Academic Press Limited: London, 61-92, (1993).
Kunitake, T., *Angew. Chem. Int. Ed. Engl.*, 31:709-726, (1992).
Martin, F.J., Specialized Drug Delivery Systems—Manufacturing and Production Technology, Marcel Dekker Inc.: New York, 267-316, (1990).
Pidgeon, C. and Venkataram, U.V., *Analytical Biochemistry*, 176:36-47, (1989).
Szoka Jr., F. and Papahadjopoulos, D., *Ann. Rev. Biophys. Bioeng.*, 9:467-508, (1980).
Tien, H.T., et al., Molecular Electronics: Biosensors and Biocomputers, Plenum Press: New York, 259-268, (1989).
Uster, S., et al., *FEBS Letters*, 386:243-246, (1996).
Zalipsky, S., *Bioconjugate Chemistry*, 4:296-299, (1993).
Zalipsky, S., et al., *FEBS Letters*, 353:71-74, (1994).
Zalipsky, S., et al., *Journal of Controlled Release*, 39:153-161, (1996).
Zalipsky, S., et al., *Bioconjugate Chemistry*, 8(2):111-118, (1997).
Zuidam, N.J., and Barenholz Y., *Biochimica et Biophysica Acta*, 1329(2):211-222, (1997).
Gabizon, A., et al., *Bioconjugate Chem.* 10:289-298, (1999).
Walde, P. and Ichikawa, S., *Biomolecular Engineering* 18:143-177, (2001).

* cited by examiner

*Primary Examiner* — Frederick Krass
*Assistant Examiner* — Isaac Shomer
(74) *Attorney, Agent, or Firm* — Robins & Pasternak LLP (57) ABSTRACT

A method of inserting a lipid-linked moiety into a lipid assembly, such as a planar lipid monolayer or bilayer, a spherical lipid vesicle, a micelle, or an emulsion envelope monolayer is described. In the method, the lipid assembly and the lipid-linked moiety are contacted in the presence of microwave irradiation to permit the lipid-linked moiety to become associated with the lipid assembly. In one embodiment, the lipid assembly is a liposome and the lipid-linked moiety is a lipid-polymer. Compositions comprised of a lipid layer and of a lipid-linked moiety, prepared in accord with the method, are also described.

2 Claims, 5 Drawing Sheets

METHOD OF LIPID STRUCTURE PREPARATION

CROSS-REFERENCE TO RELATED APPLICATIONS

This application claims the benefit of U.S. Provisional Application No. 60/617,505, filed Oct. 8, 2004, incorporated herein by reference in its entirety.

TECHNICAL FIELD

The subject matter described herein relates to a method for preparing lipid structures having a lipopolymer inserted into the outer lipid surface. The lipopolymer is incorporated into the lipid structure after formation of the lipid structure in such a way that the polymer portion of the lipopolymer extends from the lipid surface. In some embodiments, the lipopolymer includes a covalently attached diagnostic, therapeutic, or targeting ligand. More particularly, the subject matter described herein relates to a method for preparing lipid structures, such as micelles and liposomes, that have a lipopolymer, with or without a covalently attached diagnostic, therapeutic, or targeting ligand, incorporated into the lipid bilayer.

BACKGROUND

Lipid bilayers are aggregates of lipids held together by hydrophobic interactions that form a variety of different structures, such as closed spherical vesicles, planar sheets, flat discs, globules, tubes, and helices (Kunitake, T. *Angew. Chem., Int. Ed. Engl.*, 31:709 (1992)). Such lipid bilayer assemblies form spontaneously from a variety of lipids and have found use in a wide variety of technical fields. For example, planar lipid bilayer assemblies are used as optical sensors for the detection of target analytes (U.S. Pat. No. 5,616,790), as unique separation materials for peptides, proteins, nucleotides, and oligonucleotides i.e., immobilized artificial membranes (Pidgeon, C. et al., *Anal. Biochem.*, 176: 36 (1989)), as biosensors (See H. T. Tien et al. in "Molecular Electronics: Biosensors and Biocomputers", ed. F. T. Hong, Plenum Press, New York (1989) at pages 259-268), and as planar bilayer lipid membranes for studying ligand-receptor interactions at the lipid-water interface (WO 98/23948; WO 01/26800; U.S. Pat. No. 5,922,594). Spherical bilayer lipid particles, such as liposomes, have also found use as carriers of drugs or diagnostic agents.

Often it is desirable to attach or immobilize a test material or a reaction component to the lipid bilayer. For example, many types of analytical chemistry techniques rely on the immobilization of one or more of components of a reaction. Immunoassay techniques typically involve immobilizing one of the components to the lipid surface. When the test sample is washed across the lipid surface, components in the test sample having binding affinity to the immobilized component are captured for detection.

In the case of closed spherical lipid vesicles, such as micelles and liposomes, molecules are often attached to the outer vesicle surface for a variety of purposes. For example, the attached molecule can be a therapeutic agent, and attaching the agent to the lipid bilayer serves to alter the pharmacokinetics of the agent (see, for example, U.S. Pat. No. 6,326, 353). The attached molecule can be a targeting moiety that serves to direct or 'target' the vesicle to a desired site after in vivo administration (see, for example, Allen. T. M., et al., *Biochim. Biophys. Acta*, 1237:99-108 (1995); Blume, G., et al., *Biochim. Biophys. Acta*, 1149:180-184 (1993); U.S. Pat. Nos. 6,316,024; 6,214,388). Typically, the ligand is attached to the liposome surface through a linker, often a polymer chain.

Lipid vesicles having an attached ligand are typically prepared by one of several techniques. One approach involves preparation of lipid vesicles which include an end-functionalized lipid-polymer derivative; that is, a lipid-polymer conjugate where the free polymer end is reactive or "activated" (see, for example Zalipsky et al., *Bioconjugate Chem.*, 4:296 (1993); Zalipsky et al., *FEBS Letters*, 353:71 (1994); Zalipsky et al., *J. Control. Rel.*, 39:153 (1996); Zalipsky et al., *Bioconjugate Chem.*, 8(2): 111 (1997)). The lipid-activated polymer conjugate is included in the lipid mixture during liposome formation. After liposome formation, the activated polymer ends are reacted with the desired ligand (Zalipsky et al., *Bioconjugate Chem.*, 4:296 (1993)). The disadvantage to this approach is the difficulty in reacting all of the activated ends with a ligand. The approach also requires a subsequent step for separation of the unreacted ligand from the liposome composition.

In another approach, a lipid-polymer-ligand conjugate is prepared and is included in the lipid composition at the time of liposome formation (Zalipsky et al., *Bioconjugate Chem.*, 8(2):111 (1997)). This approach suffers from the disadvantage that some of the valuable ligand faces the inner aqueous compartment of the liposome and is unavailable for interaction with the intended target.

In another approach, a suspension of liposomes is incubated with a micellar suspension of lipid-polymer-ligand conjugates to achieve insertion of the conjugates into the liposomes' bilayers (see, for example, Uster et al., *FEBS Letters*, 386:243 (1996); Zalipsky et al., *Bioconjugate Chem.*, 8(2):111 (1997); U.S. Pat. Nos. 5,891,468, 6,316,024). This approach results in successful insertion of the conjugate, provided the incubation conditions are suitable and sufficient time is permitted. In some cases, the long incubation time or the required temperature to achieve insertion leads to inactivation of the ligand and/or release of liposomal contents.

Thus, there remains a need in the art for a method of attaching a desired ligand to a preformed lipid assembly.

The foregoing examples of the related art and limitations related therewith are intended to be illustrative and not exclusive. Other limitations of the related art will become apparent to those of skill in the art upon a reading of the specification and a study of the drawings.

SUMMARY

The following aspects and embodiments thereof described and illustrated below are meant to be exemplary and illustrative, not limiting in scope.

In one aspect, a method of inserting a lipid-linked moiety into a preformed lipid assembly is provided.

In another aspect, a method of inserting a lipid-polymer into a lipid bilayer assembly is provided.

In another aspect, a method of immobilizing, for a time sufficient for conducting an analytic technique or for achieving a desired end point, a lipid-linked moiety to a lipid bilayer assembly is provided.

In another aspect, a method of inserting a lipid-polymer-ligand conjugate into a lipid bilayer assembly is provided.

More specifically, and in one aspect, a method of inserting a lipid-linked moiety into a lipid assembly is described. The method comprises contacting a lipid assembly and a lipid-linked moiety in the presence of a microwave energy effective to permit the lipid-linked moiety to become associated with the lipid assembly. The lipid assembly can be a synthetic lipid assembly or a biological lipid assembly, but is preferably a synthetic lipid assembly prepared from either natural or synthetic lipids.

In various embodiments, the lipid assembly is a micelle, an emulsion envelope monolayer, a lipid bilayer, a lipid monolayer, a liposome, or the like.

In one embodiment, the lipid assembly is comprised of vesicle-forming lipids. The vesicle-forming lipids can have a phase transition temperature of greater than about 50° C., in one embodiment.

In another embodiment, the lipid-linked moiety is a lipid-polymer compound. In a preferred embodiment, the lipid-linked moiety is a lipid-polyethylene glycol compound. In other preferred embodiments, the lipid-linked moiety is a lipid-drug moiety or a lipid-biological ligand moiety. Exemplary biological ligands are peptides or proteins, such as antibodies or antibody fragments, nucleic acids molecules, including but not limited to single-stranded or double-stranded DNA or RNA oligonucleotides, polynucleotides, fragments, or the like. In one embodiment, the biological ligand has binding affinity for binding partner, such as a cell surface receptor, a blood pathogen, or the like.

In another embodiment, the lipid-linked moiety is a lipid-peptidomimetic moiety.

In another embodiment, the lipid assembly is a liposome containing an entrapped therapeutic agent. In this embodiment, the lipid-linked moiety preferably takes the form of a lipid-polymer, a lipid-biological ligand compound, or a lipid-polymer-biological ligand conjugate. Biological ligands having binding affinity for a cell surface receptor are exemplary.

In another aspect, a method of preparing a liposome composition comprised of liposomes having a lipid-linked moiety extending from the outer surface of said liposomes is described. The method includes contacting a suspension of liposomes and a micellar suspension of a lipid-linked moiety in the presence of a microwave energy source effective to permit the lipid-linked moiety to become associated with the liposomes.

In one embodiment, the microwave energy source provides between about 500-50,000 Joules, more preferably between about 10,000-40,000 Joules.

In another embodiment, the liposomes have an entrapped therapeutic agent.

In yet another embodiment, the lipid-linked moiety is a lipid-polymer moiety, such as a lipid-polyethylene glycol moiety. In another embodiment, the lipid-linked moiety is a lipid-drug moiety. In another embodiment, the lipid-linked moiety is a lipid-biological ligand moiety or a lipid-polymer-biological ligand conjugate.

In still another aspect, a lipid assembly comprised of a lipid layer and a lipid-linked moiety is disclosed. The lipid-linked moiety is stably associated with the lipid layer by virtue of exposure to a microwave source of energy. In various embodiments, the lipid-linked moiety is a lipopolymer or a lipopolymer-ligand. In one embodiment, the lipid assembly excludes liposomes.

In addition to the exemplary aspects and embodiments described above, further aspects and embodiments will become apparent by reference to the drawings and by study of the following descriptions.

BRIEF DESCRIPTION OF THE DRAWINGS

FIGS. 4A-4B show the chemical structures of fluorescent, pH-sensitive probes used to label liposomes, where

DETAILED DESCRIPTION OF THE INVENTION

I. DEFINITIONS

"Microwave" intends that section of the electromagnetic spectrum from frequencies of approximately 300 MHz to 300 GHz and wavelengths of approximately 1 meter (m) to 1 millimeter (mm). In a preferred embodiment, microwave intends frequencies of approximately 800 MHz to 300 GHz and wavelengths of approximately 37.5 centimeters (cm) to 1 millimeter (mm).

"Microwave oven irradiation" intends irradiation in a microwave oven, as exemplified by but not limited to those used to heat or cook food or drink. These ovens typically operate at about 2.45 GHz and have wavelengths ranging between 1 mm and 30 cm.

"Biologically-relevant ligand" refers to a molecule capable of specific binding to a binding partner, such as a receptor or a pathogen. Binding of the ligand to a cell receptor is typically characterized by a high binding affinity, i.e., $Km>10^5$, and can be detected by, for example, a change in the receptor's function (e.g., the opening of an ion channel) or as a change in the immediate environment of the receptor (e.g., detection of binding by surface plasmon resonance). Ligands for incorporation into lipid bilayers can be chemically synthesized, recombinantly produced, purified from cells, or obtained by other means.

"Receptor" intends a molecule capable of specifically interacting with a biologically relevant ligand. In cells, receptors are typically associated with the cellular lipid bilayer membrane. Receptors for incorporation into lipid bilayers using the techniques described herein can be chemically synthesized, recombinantly produced, purified from cells, or the like.

Binding is "specific" if it results from a molecular interaction between a binding site on a receptor and a ligand, rather than from "non-specific" sticking of one protein to another.

"Lipopolymer" is used interchangeably with "lipid-polymer" and intends a hydrophobic moiety covalently attached to a hydrophilic polymer chain. In some preferred instances, the hydrophobic moiety is a lipid having two hydrocarbon chains. A "lipid-polymer-conjugate" or "lipopolymer conjugate" refers to a lipopolymer having an attached or associated ligand. The ligand can be, for example, a biologically relevant ligand, a diagnostic ligand, a reactive moiety, a therapeutic compound, etc.

II. METHOD OF PREPARATION

A method of preparing a lipid assembly having a lipid-linked moiety incorporated therein is provided. The lipid assembly is typically one having a lipid monolayer or bilayer, collectively referred to as a lipid 'layer'. The lipid-linked moiety is incorporated into the lipid layer of the assembly in such a way that the hydrophobic portion, typically a lipid, of the lipid-linked moiety is inserted into the lipid layer of the assembly, and the opposing portion of the lipid-linked moiety extends from the surface of the assembly into, for example, an external medium. Various examples of lipid-linked moieties are discussed below. Reference to "lipid" in the term "lipid-linked" is intended to encompass any hydrophobic moiety as exemplified by lipids. The hydrophobic moiety can be a lipid having one, two, or more hydrocarbon chains or can be a hydrophobic moiety lacking a hydrocarbon chain, such as cholesterol and its analogs. Virtually any hydrophobic moiety suitable for incorporation into a lipid assembly is suitable and contemplated. The hydrophobic "lipid" is attached through a suitable chemical linkage to a selected moiety, for example, but not limited to, a drug, a polymer, a hydrophilic polymer, a protein, a peptide, a nucleic acid (RNA, DNA, single stranded, double stranded), a carbohydrate, etc. Specific non-limiting examples are given below.

The method of preparation is exemplified herein using as the lipid-linked moiety, a lipopolymer. In one embodiment, described below, the lipopolymer further includes a ligand. The ligand can be a biologically relevant ligand, a diagnostic molecule, or a reactive moiety. The ligand is typically covalently attached to the lipopolymer, but could also be "associated" with the lipopolymer, such as through electrostatic or van der Waals attraction. The ligand when covalently attached can be linked to the free terminus of the polymer in the lipopolymer, or when the lipid of the lipopolymer is a phospholipid can be attached to the third valance of the phosphodiester linkage. The ligand can be a biologically relevant ligand, having therapeutic activity or not having therapeutic activity but acting as a targeting or binding ligand. The ligand can also be a diagnostic compound, ranging from fluorescent tags to radiosensitizers. The ligand can also be a therapeutic compound, such as an organic drug. It is also contemplated that the ligand be a reactive moiety capable of reaction after the lipopolymer is incorporated into the lipid structure. Further examples of ligands are provided below.

In embodiments where the lipopolymer includes a ligand, and in particular a biologically relevant ligand, a preferred configuration is where the ligand is attached to the free terminus of the polymer in the lipopolymer. The lipid-polymer-ligand conjugate is attached to the lipid assembly by insertion of the lipid portion of the conjugate into the lipid layer of the assembly using the method described hereinbelow. Preferably, a plurality of lipid-polymer-ligand conjugates are inserted into the lipid layer; however, it will be appreciated that the number or density of attached conjugates can be controlled by selection of the ratio of conjugate lipid to layer lipid, as more fully described below. The inserted lipopolymer conjugate remains associated or immobilized within the lipid layer assembly for a time sufficient to achieve an end result, such as completing an assay or binding to a desired target.

Lipid layers are readily formed by a variety of techniques and from a wide range of lipids and lipid mixtures. Preparation of planar lipid bilayers is described, for example, in Hanke, W. and Schlue, W. R., Planar Lipid Bilayers, D. B. Sattelle, Ed., Academic Press (1993) and in WO 98/23948. Preparation of lipid vesicles is described, for example, in Szoka F. and Papahadjopoulos, D. *Ann. Rev. Biophys. Bioeng.*, 9:467 (1980). The lipids in the lipid layer can comprise natural lipids purified from biological membranes and/or synthetic lipids. Examples of natural lipids include but are not limited to Azolectin, a commercially available lipid extract from soybeans (Sigma, St. Louis, Mo.), and phosphatidylcholine and phosphatidylethanolamine purified from egg yolk. Synthetic lipids can be lipids which are pure in their head-group and hydrocarbon composition or lipids that are not normally present in biological membranes. Preferred lipids include 'vesicle-forming lipids', which refers to any lipid capable of forming part of a stable micelle or liposome composition and typically including one or two hydrophobic, hydrocarbon chains or a steroid group and may contain a chemically reactive group, such as an amine, acid, ester, aldehyde or alcohol, at its polar head group. Exemplary synthetic and natural vesicle-forming lipids are given below.

In the method, a lipid assembly, typically a lipid monolayer or bilayer, is prepared. The lipid assembly can be supported on a lipid layer-compatible surface or substrate, such as an oxidized silicon wafer or a fused silica wafer, treated as needed to be form and support a lipid layer. Alternatively, the lipid assembly can be self-supporting, i.e., not supported on a substrate, such as in a micelle or a liposome or an emulsion envelope monolayer.

In one study, liposomes containing doxorubicin were prepared and incubated for various times in a microwave oven, as described in Example 1. Stability of the liposomes was assessed by measuring the amount of doxorubicin released from the liposomes after exposure to the microwave energy and by measuring the amount of liposomal doxorubicin after such exposure. Additionally, the size of the liposomes before and after incubation in the presence of microwave energy was measured.

The results showed that incubation in the presence of microwave irradiation of doxorubicin-containing liposomes for times of 30, 45, 60, and 90 seconds did not induce release of the drug from the liposomes. Nor did such incubation cause a change in liposome particle size. Before and after the microwave incubation, the liposomal doxorubicin concentration was 3.8 mM and the liposome diameter was 90 nm. Thus, liposome integrity was not compromised by microwave irradiation for times up to 90 seconds, at the power level used (510 W; total energy of 45.9 kJ).

Example 2 describes a study where microwave irradiation was used to facilitate insertion of a lipid-polymer-targeting ligand conjugate into pre-formed liposomes. Liposomes were prepared as described in Example 1A and were composed of HSPC, cholesterol, and mPEG-DSPE. A lipid-polymer-ligand conjugate comprised of DSPE-PEG-ligand was prepared as described in Example 2A. The ligand was a single chain Fv (scFv) antibody fragment having binding affinity for c-erbB-2 receptor epitope (WO 99/55367). A micellar suspension of the DSPE-PEG-scFv conjugate and a suspension of the liposomes were mixed at a fixed concentration of 6 µg scFv ligand per µl mole phospholipid, at a total phospholipid concentration of 47 µmole/mL. The mixture was subjected to various conditions, including temperature, solvent (ethanol), ultrasonic irradiation, time, and microwave irradiation, and the extent of insertion of conjugate into the liposomal lipid bilayer was analyzed. The incubation conditions and insertion results are summarized in Table 1.

TABLE 1

Effect of temperature, addition of ethanol, and microwave oven irradiation on DSPE-PEG-scFv conjugate insertion into placebo liposomes

| Conditions | | | | Free Conjugate | Conjugated | Total Conjugate |
|---|---|---|---|---|---|---|
| Microwave | Temperature | Time | Ethanol | (not inserted) | (inserted) | (recovered) |
| − | RT* | 1 hour | − | 100% | 0% | 100% |
| − | RT | 3 hour | − | 100% | 0% | 100% |
| − | RT | 72 hour | − | − | − | − |
| − | RT | 1 hour | 0.10% | 100% | 0% | 100% |
| − | RT | 3 hour | 0.10% | 100% | 0% | 100% |
| − | RT | 72 hour | 0.10% | − | − | − |
| − | RT | 1 hour | 0.50% | 100% | 0% | 100% |
| − | RT | 3 hour | 0.50% | 100% | 0% | 100% |
| − | RT | 24 hour | 0.50% | 100% | 0% | 100% |
| − | 37° C. | 1 hour | − | 100% | 0% | 100% |
| − | 37° C. | 3 hour | − | 100% | 0% | 100% |
| − | 37° C. | 72 hour | − | 100% | 0% | 100% |
| − | 37° C. | 1 hour | 0.10% | 100% | 0% | 100% |
| − | 37° C. | 3 hour | 0.10% | 100% | 0% | 100% |
| − | 37° C. | 72 hour | 0.10% | 0% | 0% | 100% |
| − | 37° C. | 1 hour | 0.50% | 100% | 0% | 100% |
| − | 37° C. | 3 hour | 0.50% | 100% | 0% | 100% |
| − | 37° C. | 24 hour | 0.50% | 36% | 64% | 100% |
| − | 60° C. | 1 hour | − | 27% | 73% | 100% |
| + | | 30 sec | − | 23% | 77% | 100% |
| + | | 45 sec | − | 19% | 81% | 100% |
| + | | 1 min | − | 12.40% | 87.6% | 100% |
| + | | 1.5 min | − | 11.70% | 88.3% | 100% |
| + | | 3 min | − | 50% | 50% | 100% |
| + | | 10 min | − | 0% | 100% | 50% |

*RT = room temperature (22-25° C.);
− = not done or not added;
+ = done

Table 1 shows that incubation at room temperature and at 37° C. for up to 72 hours did not result in insertion of the DSPE-PEG-scF5 conjugate into the liposomal lipid bilayers. Addition of ethanol at 0.1% and at 0.5% did not facilitate insertion of the conjugate into the liposomal bilayers, except for the sample incubated at 37° C. for 24 hours. Incubation of the targeting conjugate with liposomes at 60° C. for 1 hour resulted in 73% of the conjugate being inserted into the liposomal bilayers (27% of the conjugate free, uninserted). Incubation of the conjugate and liposomes for 10 minutes and 20 minutes in a sonication bath at room temperature did not result in insertion of the conjugate into the liposomes (not shown in Table 1).

Figure 1A:
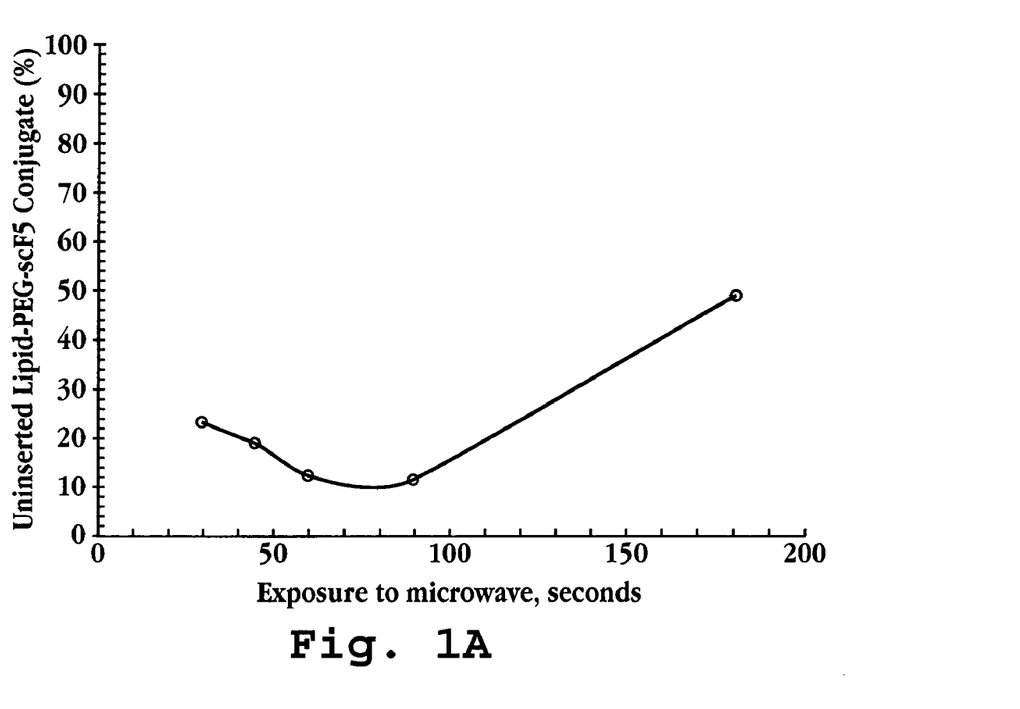
FIG. 1A is a plot showing the percentage of lipid-polymer-targeting ligand conjugate in free form uninserted into the lipid bilayer of pre-formed liposomes, after incubation of the conjugate with the pre-formed liposomes in the presence of microwave irradiation for various times.
Figure 1B:
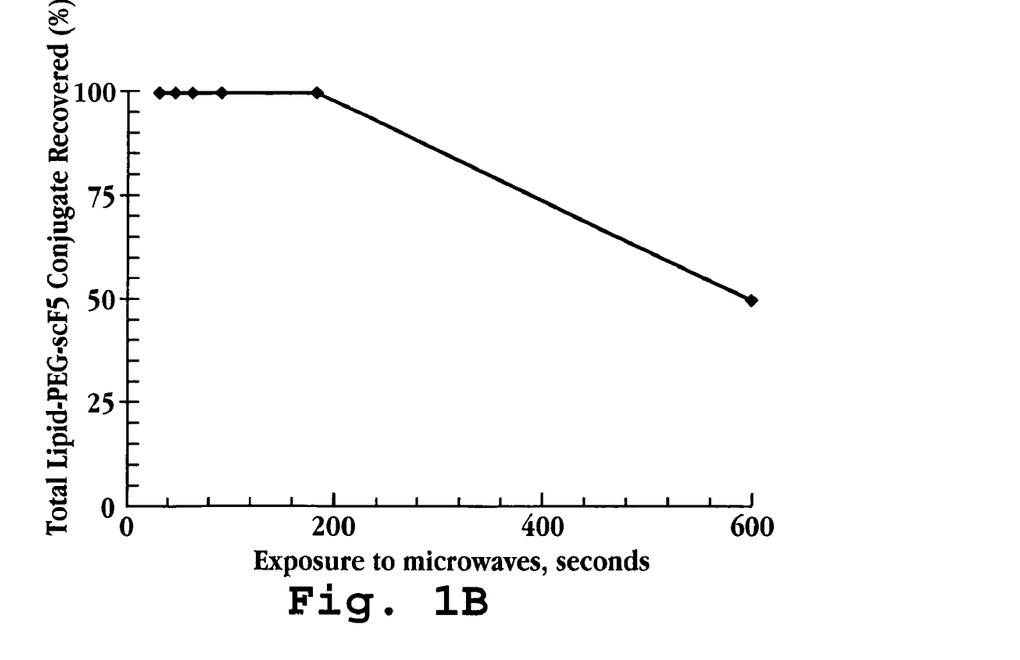
FIG. 1B is a plot showing the total percentage of lipid-polymer-targeting ligand conjugate recovered after incubation with pre-formed liposomes in the presence of microwave irradiation for various times.

With continuing reference to Table 1, incubation with exposure to microwave irradiation of between 30 second and 90 seconds lead to high insertion levels, with more than 80% of the free conjugate inserted after 45 seconds of microwave irradiation and less than 90 seconds irradiation, without conjugate loss at the energy level employed. FIG. 1A plots the results for the samples incubated in the presence of microwave irradiation, where the amount of free, uninserted DSPE-PEG-scFv lipopolymer conjugate is plotted against the time of exposure to microwave irradiation in a microwave oven. FIG. 1B is a related plot, showing the total free, uninserted DSPE-PEG-scFv conjugate in the incubation medium as a function of microwave incubation time. FIG. 1A shows that a 30 second exposure to 510 W from a microwave source caused 77% insertion of the lipopolymer conjugate into the liposomes, without any lipopolymer conjugate loss (see, final Col. of Table 1; FIG. 1B). It is worth noting as a point of comparison that a similar extent of insertion was also achieved after heating at 60° C. for one hour (see Table 1). Further increase of microwave irradiation exposure time to 90 seconds lead to insertion of 88% of the lipopolymer conjugate without any loss of total conjugate amount. Microwave irradiation for 3 minutes at this power level resulted in a lower (50%) insertion amount without loss of total lipopolymer conjugate amount. Microwave irradiation for 10 minutes lead to the degradation of 50% of the lipopolymer conjugate. This profile of insertion was obtained for all sample volumes (200-1000 μL) tested.

The stability of the immunoliposomes prepared by microwave insertion of the DSPE-PEG-scFv lipopolymer conjugate was assessed by monitoring the concentration of free lipopolymer conjugate in the liposome suspension medium for one month. Samples were taken periodically and analyzed by high pressure liquid chromatography for the presence of free lipopolymer conjugate. As a control, a micellar suspension of DSPE-PEG-scFv conjugate was subjected to identical microwave irradiation conditions (1 minute irradiation at 580 W=34.8 kJ) in the absence of liposomes. The results are shown in Tables 2A-2B, where the total amount (liposome-bound and free) of DSPE-PEG-scFv conjugate, the free amount of DSPE-PEG-scFv conjugate in the suspension medium, the percentage of free DSPE-PEG-scFv conjugate from the total (Table 2A), and the total amount of DSPE-PEG-scFv conjugate alone exposed to microwave irradiation in the absence of liposomes (Table 2B), are summarized.

TABLE 2A

Stability of Immunoliposomes Prepared by Microwave Insertion

DSPE-PEG-scFv Conjugates Incubated with Liposomes in Presence of Microwave Irradiation

| No. of days at 4° C. | Total Conjugate Conc. (μg/mL) | *Conc. Of Free (Non-liposomal) Conjugate, (μg/mL) | Percent of Free Conjugate (%) |
|---|---|---|---|
| 0 | 267.6 | 56.5 | 21.1 |
| 1 | 206.9 | 37.8 | 18.3 |

TABLE 2A-continued

Stability of Immunoliposomes Prepared by Microwave Insertion

DSPE-PEG-scFv Conjugates Incubated with Liposomes in Presence of Microwave Irradiation

| No. of days at 4° C. | Total Conjugate Conc. (µg/mL) | *Conc. Of Free (Non-liposomal) Conjugate, (µg/mL) | Percent of Free Conjugate (%) |
|---|---|---|---|
| 4 | 254.8 | 48.1 | 18.9 |
| 5 | 257.3 | 53.9 | 21.0 |
| 6 | 252.2 | 49.4 | 19.6 |
| 8 | 229.6 | 57.8 | 25.2 |
| 11 | 240.0 | 57.8 | 24.1 |
| 13 | 211.0 | 112.5 | 53.3 |

*Average of two measurements

TABLE 2B

Stability of Lipid-Polymer-Ligand Conjugate in the Absence of Liposomes to the Exposure to Microwave Irradiation DSPE-PEG-scFv Conjugates Incubated without Liposomes in Presence of Microwave Irradiation

| No. of days at 4° C. | *Total Conjugate Conc. (µg/mL) | Percent of Conjugate (%) |
|---|---|---|
| 0 | 629 | 100 |
| 1 | 589 | 100 |
| 4 | 620 | 100 |
| 5 | 650 | 100 |
| 6 | 598 | 100 |
| 8 | 690 | 100 |
| 11 | 650 | 100 |
| 13 | 624 | 100 |
| 14 | 632 | 100 |
| 18 | 610 | 100 |
| 30 | 635 | 100 |

*Average of two measurements

Table 2A shows that DSPC-PEG-scFv conjugate inserted to the liposomes by one minute exposure to microwave irradiation was stable and remained stably inserted for 8-11 days when kept at 4° C. During this period, the concentration of free conjugate (not associated with a liposomal bilayer) was about 20% of total conjugate amount. After about 11 days, further storage at 4° C. led to an increased level of free conjugate in the suspension medium without loss. Table 2B shows that the lipid-polymer-ligand conjugate is stable and apparently unaffected by exposure for one minute to microwave irradiation.

Figure 2A:
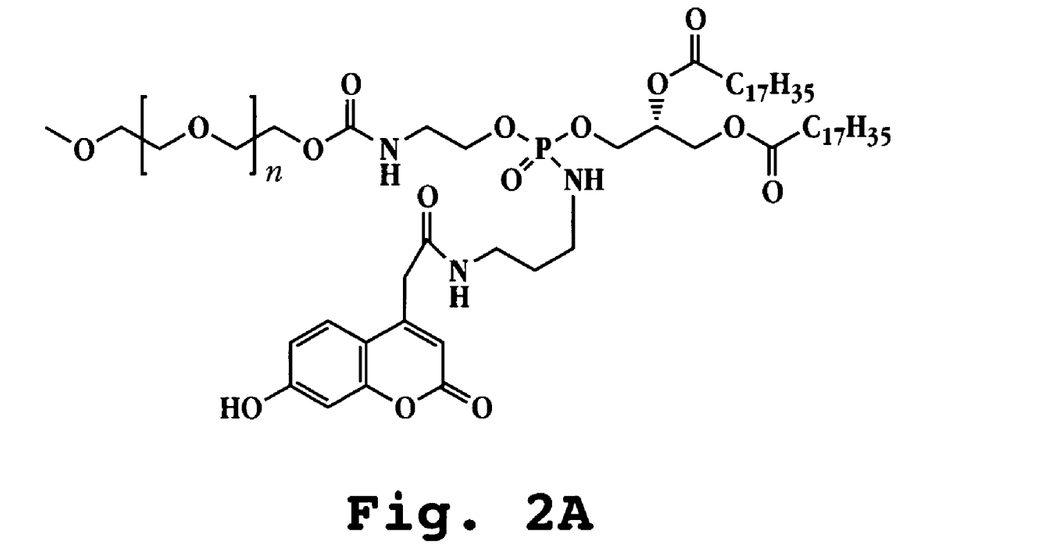
FIG. 2A shows the chemical structure of a fluorescent lipopolymer, DSPE-HC-PEG.

In another study, the method of microwave irradiation was used to insert a lipid-polymer ("lipopolymer") conjugate into pre-formed liposomes, where the lipopolymer conjugate was a PEG-DSPE lipopolymer with 4-hydroxycoumarin (HC) linked to the free valence of the phosphodiester of DSPE. The conjugate, shown in FIG. 2A, was prepared according to the reaction scheme described in Example 3A and illustrated in FIG. 2B. In aqueous solutions, the lipopolymer conjugate, DSPE-HC-PEG, has little fluorescence below its critical micelle concentration (~3 µM), and upon insertion into lipidic environments, such as micelles or liposomes, its fluorescent intensity increases in proportion to the amount of inserted lipopolymer conjugate. Thus, it acts as a diagnostic ligand, or probe, to determine insertion of a compound into a lipidic environment.

Placebo liposomes were mixed with a solution of PEG-HC-DSPE and then exposed to microwave irradiation in the microwave oven operated at a capacity to provide 510 W of power for 15, 30, 45 and 60 seconds (Example 3B). Immediately after this exposure time, fluorescence was measured. Fluorescence was also measured every hour for five hours and 21 hours after the exposure to microwave irradiation. The results are shown in FIG. 3.

Figure 3:
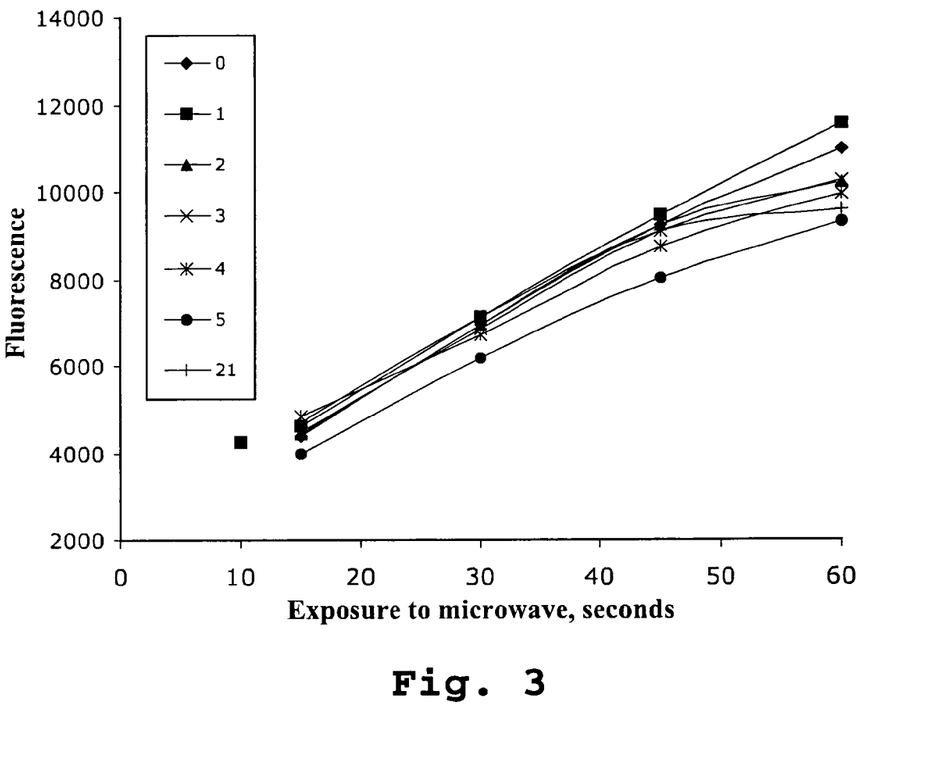
FIG. 3 is a plot of fluorescent intensity as a function of time of microwave irradiation time, in seconds, of a suspension of fluorescently-labeled liposomes incubated with a conjugate of DSPE-PEG, where the liposomal-bound fluorophore fluoresces in response to changes in charge density.

Insertion of the lipid-polymer conjugate into the liposomes increased with longer microwave irradiation exposure times, as seen in FIG. 3. There was little change in fluorescence intensity after exposure to microwave irradiation, as evidenced by the fluorescence intensity at the one hour intervals from 1-5 hours post microwave radiation. Also, the absolute value of fluorescence for each incubation time did not significantly change after storage for 21 hours, indicating that the inserted fluorescent conjugate remained in the liposome bilayer.

The extent of insertion of the fluorescent PEG-HC-DSPE lipopolymer conjugate after 60 second exposure to microwave irradiation was measured using SEC-HPLC, and it was determined that 85% of the total quantity of fluorescent lipopolymer conjugate was inserted into the liposomes.

Figure 4A:
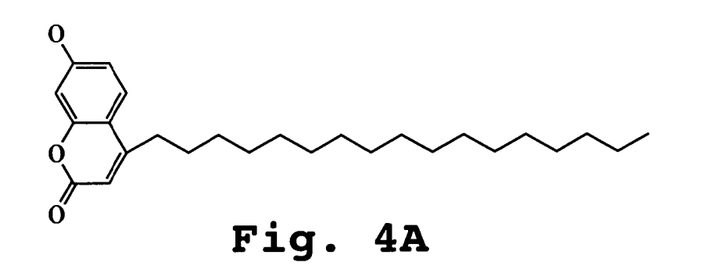
FIG. 4A shows the structure of 7-heptadecyl-4-hydroxycoumarin ($C_{17}HC$) and FIG. 4B shows the structure of or 1,2-dioleoyl-sn-glycero-3-phosphoethanolamine (DOPE-HC).
Figure 4B:
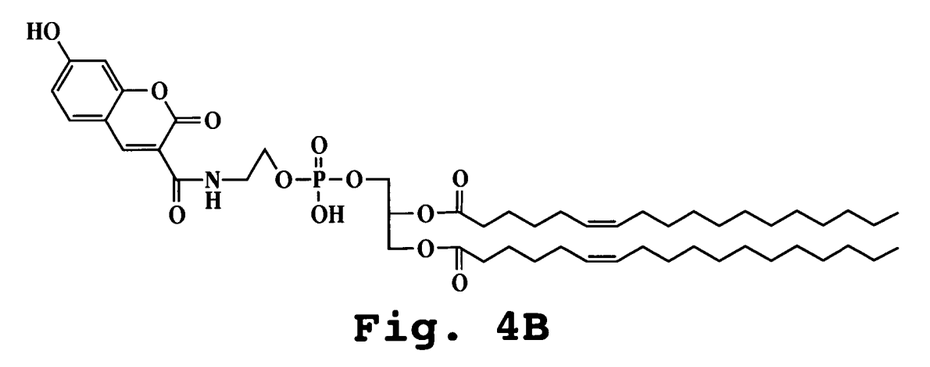

More generally, and as noted above, the method of microwave irradiation can also be used to insert a lipid-polymer ("lipopolymer"), that is a lipopolymer lacking any ligand, into a pre-formed lipid structure, such as liposomes. This general concept was illustrated in another study, described in Example 4, where liposomes having a lipid bilayer of egg phosphatidylcholine and including a fluorescent label were incubated with a micellar suspension of the lipopolymer DSPE-PEG. Two studies were done, using two different fluorescent labels, shown in FIGS. 4A-4B, incorporated into the liposome lipid bilayers. FIG. 4A shows the structure of 7-heptadecyl-4-hydroxycoumarin ($C_{17}HC$) and FIG. 4B shows the structure of 1,2-dioleoyl-sn-glycero-3-phosphoethanolamine (DOPE-HC). A small amount of one of the fluorescent lipidic labels was included in the lipids during formation of the liposomes. DSPE-PEG lipopolymer micelles were added to the liposomes and the mixture was exposed to 90 seconds microwave irradiation (510 W), then the quantity of inserted DSPE-PEG was determined by the shift in apparent pKa of the HC moiety.

The results for liposomes labeled with $C_{17}HC$ are shown in Table 3. In this study, as a comparative point of reference, the insertion of DSPE-PEG (MW 2000 Daltons) lipopolymer into the same liposomes at room temperature (no microwave irradiation) was also measured.

TABLE 3

Apparent pKa of $C_{17}HC$ in EPC liposomes before and after insertion of 2000 PEG-DSPE.

| Sample No. | Liposomes and Incubation Conditions | apparent pKa |
|---|---|---|
| 1 | EPC without PEG-DSPE | 9.41 |
| 2 | EPC with PEG-DSPE (90 sec in MW) immediately | 9.98 |
| 3 | EPC with PEG-DSPE (5 hours at RT) | 10.13 |
| 4 | EPC with PEG-DSPE (90 sec in MW) after 48 hours | 10.28 |
| 5 | EPC with PEG-DSPE (5 hours at RT) after 48 hours | 10.14 |

Table 3 shows that 90 seconds of exposure to microwave irradiation and 5 hours of room temperature incubation increase pKa values to a similar extent, suggesting similar level of insertion. The increasing pKa of $C_{17}HC$ shows that the DSPE-PEG lipopolymer was inserted into the liposome bilayer and that the liposome surfaces became more negatively charged. The apparent pKa values of $C_{17}HC$ were also measured 48 hours after the incubation periods, and showed that the electrical surface potential of the liposomes did not change significantly, indicating the inserted lipopolymer remained associated with the liposomes.

With respect to the liposomes labeled with DOPE-HC, the results are shown in Table 4. The DOPE-HC-labeled egg PC liposomes were incubated with DSPE-PEG (MW 2000 Daltons) conjugates in the presence of microwave irradiation for 90 seconds. The extent of lipopolymer insertion was calculated from the apparent pKa, as described in Example 4.

TABLE 4

Apparent pKa of DOPE-HC in EPC liposomes before and after insertion of 2000 PEG-DSPE Lipopolymer.

| No | Liposome Composition and Incubation Conditions | apparent pKa |
|---|---|---|
| 1 | EPC without PEG-DSPE or PEG | 9.12 |
| 2 | EPC with PEG-DSPE (90 sec in MW) immediately | 9.26 |
| 3 | EPC with PEG (90 sec in MW) immediately | 9.09 |
| 4 | EPC without PEG-DSPE or $^{2000}$PEG, after 48 hours | 9.28 |
| 5 | EPC with PEG-DSPE (90 sec in MW) after 48 hours | 9.38 |
| 6 | EPC with PEG (90 sec in MW) after 48 hours | 9.08 |

The relative changes in apparent pKa are qualitatively the same for those measured for the study conducted with $C_{17}$HC-labeled liposomes (Table 3), with lower absolute values. These lower values reflect the further away (from the surface) location of the fluorophore for DOPE-HC compared to $C_{17}$HC. After 48 hours of storage at room temperature, the apparent pKa values of the liposomes did not change significantly (results not shown), indicating the lipopolymer remained associated with the liposome bilayer.

Also in this study, a sample of the EPC liposomes was combined with free polyethylene glycol (PEG, MW 2000 Daltons) and exposed for 90 seconds to microwave irradiation in the microwave oven at 60% capacity (850 W total capacity). No insertion of free PEG (i.e., PEG lacking a lipidic or hydrophobic portion) into liposomes was observed.

It will be apparent to those of skill that the microwave irradiation method can be used to insert virtually any lipid-linked moiety into a pre-formed lipid assembly. The examples above illustrate insertion via microwave irradiation of a lipid-linked moiety, where the lipid-linked moiety is a lipid-polymer or a lipid-polymer-ligand. The lipid-linked moiety can also be a lipid-ligand moiety. The lipid assembly can be any lipid structure, preferably comprised primarily of synthetic lipids and having a lipid bilayer. However, the lipid assembly can also be comprised of natural or biological lipids, and can be a lipid monolayer.

While the foregoing examples relied on a lipopolymer or a lipopolymer-ligand conjugate to illustrate the method of preparation, it will be appreciated that a variety of lipid-linked moieties are contemplated, and that the lipopolymer is merely exemplary. For example, a therapeutic drug (such as those listed below) can be attached to a hydrophobic moiety and inserted into a lipidic structure. Peptides, proteins, nucleic acids, carbohydrates can also be attached to hydrophopic moieties and then inserted into a lipidic structure. Attachment of these exemplary moieties to a selected lipid is well within the routine skill of a chemist.

III. UTILITY

The insertion method of the present invention finds use in attaching or inserting a wide variety of lipopolymers and lipopolymer-ligand conjugates to lipid assemblies. The lipid assembly can be in the form of closed spherical vesicle, a planar sheet, a flat disc, a globule, a tube, or a helix. In preferred embodiment, the lipid assembly is a lipid vesicle or a lipid planar sheet.

1. Bilayer Lipid Vesicles

Bilayer lipid vesicles, also referred to as liposomes, are spherical particles comprised of concentrically ordered lipid bilayers that encapsulate an aqueous phase. Liposomes can serve as a delivery vehicle for therapeutic or diagnostic agents contained in the aqueous phase or in the lipid bilayers. Delivery of drugs in liposome-entrapped form can provide a variety of advantages, depending on the drug, including, for example, a decreased drug toxicity, altered pharmacokinetics, or improved drug solubility. Liposomes when formulated to include a surface coating of hydrophilic polymer chains, so-called Stealth® or long-circulating liposomes or sterically stabilized liposomes, offer the further advantage of a long blood circulation lifetime, due in part to reduced removal of the liposomes by the mononuclear phagocyte system (see U.S. Pat. No. 5,013,556). Often an extended lifetime is necessary in order for the liposomes to reach their desired target region or cell from the site of injection.

In accord with the method described herein, liposomes having an outer surface coating of hydrophilic polymer chains can be prepared. As described above, lipopolymers are inserted into pre-formed liposomes during exposure to microwave irradiation. The lipopolymers are incorporated into the outer lipid bilayer such that the lipid portion of the lipopolymer is inserted into the liposomal lipid bilayer and the polymer portion of the lipopolymer extends away from the liposomal surface into the external medium.

Liposomes having a targeting, therapeutic, and/or diagnostic ligand, so-called "immunoliposomes", can also be prepared using the method described herein. As noted above, the attached ligand can be a therapeutic agent, such as a small molecule that has a short blood circulation lifetime, or a targeting moiety that directs the liposome, and any entrapped payload, to a specific tissue or cell. The ligand is attached or associated with the lipid-polymer, typically by attachment to the free terminus of the polymer or attached to the free valence of the phosphodiester when the lipid is a phospholipid.

Liposomes suitable for use in the present method include those composed primarily of vesicle-forming lipids. Vesicle-forming lipids refer to lipids that spontaneously form lipid bilayers above their gel to liquid crystalline phase transition temperature range. Such lipids typically have certain features that permit spontaneous bilayer formation, such as close to identical cross section areas of their hydrophobic and hydrophilic portions permitting packing into lamellar phases. Lipids capable of stable incorporation into lipid bilayers, such as cholesterol and its various analoges, can be incorporated into the lipid bilayer during bilayer formation. The vesicle-forming lipids are preferably lipids having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and either saturated or having varying degrees of unsaturation. The above-described lipids and phospholipids whose acyl chains have varying degrees of saturation can be obtained commercially or prepared according to published methods. Other suitable lipids include phospholipids, sphingolipids, glycolipids, and sterols, such as cholesterol.

Cationic lipids can also be employed, and the cationic lipid can be included either as a minor component of a lipid mixture or as a major or sole component, which form the liposomes. Cationic lipids typically have a lipophilic moiety, such as a sterol, an acyl or diacyl chain, and where the lipid has an overall net positive charge. Preferably, the head group of the lipid carries the positive charge. Exemplary monocationic lipids include 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 3 [N—(N',N'-dimethylaminoethane) carbamoly] cholesterol (DC-Chol); and dimethyldioctadecylammonium (DDAB).

Another group are the polycationic lipids, such as DOSPA, DOGS, and others, that by themselves form micelles and in the presence of other lipids such as cholesterol or dioleoylphosphatidyl ethanolamine (DOPE) form liposomes. Other polycationic lipids may be a neutral lipid, such as dioleoylphosphatidyl ethanolamine (DOPE) or other phospholipids, derivatized with a polycationic molecule, such as polylysine or other polyamines, such as spermine.

The vesicle-forming lipid can be selected to achieve a specified degree of fluidity or rigidity, to control the stability of the liposome in serum, to control the conditions effective for insertion of the targeting conjugate, as will be described, and/or to control the rate of release of the entrapped agent in the liposome. Liposomes having a more rigid lipid bilayer, or a gel state (solid ordered) phase bilayer, are achieved by using a relatively rigid lipid, e.g., a lipid having long and saturated acyl chains and, therefore, a relatively high phase transition temperature range, e.g., >37° C. up to 60° C. Such lipids contribute to a greater membrane rigidity in the lipid bilayer. Other lipid components, such as cholesterol, are also known to contribute to membrane rigidity in lipid bilayer structures by transforming the bilayer to be in a liquid ordered phase.

On the other hand, high lipid fluidity is achieved by incorporation of a relatively fluid lipid, typically one having a lipid phase with a relatively low liquid to liquid-crystalline phase transition temperature range, e.g., at or below 37° C. These may be either lipids having two main medium chains (C14), hydrocarbon chain, or those having one or two unsaturated hydrocarbon chains.

The liposomes can also include a vesicle-forming lipid derivatized with a hydrophilic polymer to form a lipopolymer that is no a vesicle-forming lipid. As has been described, for example in U.S. Pat. No. 5,013,556, including such a derivatized lipid in the liposome composition forms a surface coating of hydrophilic polymer chains around the liposome. The surface coating of hydrophilic polymer chains is effective to increase the in vivo blood circulation lifetime of the liposomes when compared to liposomes lacking such a coating.

Vesicle-forming lipids suitable for derivatization with a hydrophilic polymer include any of those lipids listed above, and, in particular phospholipids, such as distearoyl phosphatidylethanolamine (DSPE).

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences. The polymers may be employed as homopolymers or as block or random copolymers.

A preferred hydrophilic polymer chain is polyethyleneglycol (PEG), preferably as a PEG chain having a molecular weight between 500-10,000 daltons, more preferably between 750-10,000 daltons, still more preferably between 750-5000 daltons. Methoxy or ethoxy-capped analogues of PEG are also preferred hydrophilic polymers, commercially available in a variety of polymer sizes, e.g., 120-20,000 daltons.

Preparation of vesicle-forming lipids derivatized with hydrophilic polymers has been described, for example in U.S. Pat. No. 5,395,619. Preparation of liposomes including such derivatized lipids has also been described, where typically between 1-20 mole percent of such a derivatized lipid is included in the liposome formulation (see, for example, U.S. Pat. No. 5,013,556). In brief, liposomes are prepared by a variety of techniques, such as those detailed in Szoka, F., Jr., et al., *Ann. Rev. Biophys. Bioeng.,* 9:467 (1980), and specific examples of liposomes prepared in support of the present invention were given above. Typically, the liposomes are multilamellar vesicles (MLVs), which can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The liposomes can include a vesicle-forming lipid derivatized with a hydrophilic polymer to form a surface coating of hydrophilic polymer chains on the liposomes surface. Addition of between about 1-20 mole percent of a lipid-polymer conjugate to the lipid mixture at the time of liposome formation results in polymer chains extending from both the inner and outer surfaces of the liposomal lipid bilayers. Exemplary methods of preparing polymer-derivatized lipids and of forming polymer-coated liposomes have been described in U.S. Pat. Nos. 5,013,556, 5,631,018 and 5,395,619, which are incorporated herein by reference. It will be appreciated that the hydrophilic polymer may be stably coupled to the lipid, or coupled through an unstable linkage, which allows the polymer coated liposomes to shed the coating of polymer chains as they circulate in the bloodstream or in response to a stimulus.

The liposomes also include a therapeutic or diagnostic agent, and exemplary agents are provided below. The selected agent is incorporated into liposomes by standard methods, including (i) passive entrapment of a water-soluble compound by hydrating a lipid film with an aqueous solution of the agent, (ii) passive entrapment of a lipophilic compound by hydrating a lipid film containing the agent, and (iii) loading an ionizable drug against an inside/outside liposome pH gradient. Other methods, such as reverse-phase evaporation, are also suitable.

After liposome formation, the liposomes can be down sized to obtain a population of liposomes having a substantially homogeneous size range, typically between about 0.01 to 0.5 microns, more preferably between 0.03-0.40 microns. One effective sizing method for REVs and MLVs involves extruding an aqueous suspension of the liposomes with or without ethanol through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. In many cases extrusion is done stepwise starting with a large pore size filter. Homogenization methods are also useful for down-sizing liposomes to sizes of 100 nm or less (Martin, F. J., in SPECIALIZED DRUG DELIVERY SYSTEMS—MANUFACTURING AND PRODUCTION TECHNOLOGY, P. Tyle, Ed., Marcel Dekker, New York, pp. 267-316 (1990)).

After formation of the liposomes, a lipid-linked moiety is incorporated into the lipid bilayer using the microwave irradiation method described herein. Typically, a plurality of lipid-linked moieties, the same or different, are incorporated into the lipid bilayer. The pre-formed liposomes and the lipid-linked moiety are mixed and then exposed to microwave irradiation to achieve insertion of the lipid-linked moiety into the outer liposome bilayer leaflet. Insertion of the lipid-linked moiety results in the lipid portion of being anchored into the lipid bilayer of the lipid assembly, with the opposing portion of the lipid-linked moiety (i.e, the "moiety") being oriented outwardly from the lipid surface, thus providing an outer surface coating of the "moiety". In embodiments where a ligand is attached to the lipid-linked moiety, as in a lipopolymer-ligand conjugate or a lipid-drug-ligand conjugate, the ligand is also oriented outwardly from the lipid surface and therefore available for interaction with its cognate receptor or binding partner.

It will be appreciated that the irradiation conditions effective to achieve insertion of the lipid-linked moiety into the lipid structure are determined based on several variables, including, the desired rate of insertion, the temperature to which a given moiety can be safely heated without detrimental effect, for example on its binding or therapeutic activity, and to a lesser degree the phase transition temperature of the lipids and the lipid composition.

As noted above, a ligand can be a molecule that has binding affinity for a cell receptor, a pathogen circulating in the blood, or the like. The ligand can also be a therapeutic or diagnostic molecule, in particular molecules that when administered in free form have a short blood circulation lifetime.

In one embodiment, the ligand is a biological ligand, and preferably is one having binding affinity for a cell receptor. Exemplary biological ligands are molecules having binding affinity to receptors for CD4, folate, insulin, LDL, vitamins, transferrin, asialoglycoprotein, selectins, such as E, L, and P selectins, Flk-1,2, FGF, EGF, integrins, in particular, $\alpha_4\beta_1$ $\alpha_1\beta_3$, $\alpha_v\beta_1$ $\alpha_v\beta_5$, $\alpha_v\beta_6$ integrins, HER2, and others. Preferred ligands include proteins and peptides, including antibodies and antibody fragments, such as $F(ab')_2$, $F(ab)_2$, Fab', Fab, Fv (fragments consisting of the variable regions of the heavy and light chains), and scFv (recombinant single chain polypeptide molecules in which light and heavy variable regions are connected by a peptide linker), and the like. The ligand can also be a small molecule peptidomimetic.

It will be appreciated that a cell surface receptor, or fragment thereof, can serve as the ligand.

The ligand is readily attached to a lipid or to a polymer-derivatized lipid using synthetic reaction schemes published in the literature (U.S. Pat. No. 6,180,134; Zalipsky, S. et al., FEBS Lett., 353:71 (1994); Zalipsky et al., Bioconjugate Chem., 4:296 (1993); Zalipsky et al., J. Control. Rel., 39:153 (1996); Zalipsky et al., Bioconjugate Chem., 8(2):111 (1997)). The linkage between the ligand and the polymer or lipid can be a stable covalent linkage or a releasable linkage that is cleaved in response to a stimulus, such as a change in pH or presence of a reducing agent, and/or molecules containing —SH moieties.

The liposomes can also include a therapeutic or diagnostic agent in entrapped form. Entrapped is intended to include encapsulation of an agent in the aqueous core and aqueous spaces of liposomes as well as entrapment of an agent in the lipid bilayer(s) of the liposomes. Agents contemplated for use in the composition of the invention are widely varied, and non-limiting examples of agents suitable for therapeutic and diagnostic applications include steroids, immunosuppressants, antihistamines, non-steroidal anti-asthamtics, non-steroidal anti-inflammatory agents, cyclooxygenase-2 inhibitors, cytotoxic agents, antiviral agents, gene therapy agents, radiotherapy agents, and imaging agents.

The entrapped therapeutic agent is, in one embodiment, a cytotoxic drug. The drug can be an anthracycline antibiotic, including but not limited to doxorubicin, daunorubicin, epirubicin, and idarubicin, including salts and analogs thereof. The cytotoxic agent can also be a platinum compound, such as cisplatin, carboplatin, ormaplatin, oxaliplatin, zeniplatin, enloplatin, lobaplatin, spiroplatin, ((−)-(R)-2-aminomethylpyrrolidine (1,1-cyclobutane dicarboxylato)platinum), (SP-4-3(R)-1,1-cyclobutane-dicarboxylato(2-)-(2-methyl-1, 4-butanediamine-N,N')platinum), nedaplatin and (bis-acetato-ammine-dichloro-cyclohexylamine-platinum(IV)).

The cytotoxic agent can also be a topoisomerase 1 inhibitor, including but not limited to topotecan, irinotecan, (7-(4-methylpiperazino-methylene)-10,11-ethylenedioxy-20(S)-camptothecin), 7-(2-(N-isopropylamino)ethyl)-(20S)-camptothecin, 9-aminocamptothecin and 9-nitrocamptothecin. The cytotoxic agent can also be a vinca alkaloid such as vincristine, vinblastine, vinleurosine, vinrodisine, vinorelbine, and vindesine. The entrapped therapeutic agent can also be an angiogenesis inhibitor, such as angiostatin, endostatin and TNFα.

2. Planar Lipid Bilayers

In another embodiment, the lipid bilayer is a planar lipid bilayer expanse supported on a suitable substrate. Planar lipid bilayer are established using techniques known in the art. For example, a substrate of glass, quartz, mica, or the like is chosen and a phospholipid bilayer is deposited either one leaflet at a time from an air-water interface or by fusion of preformed liposomes (Groves, J. and Dustin, M., J. Immunological Mtds, 278:19 (2003)). The bilayer can be formed on the substrate in a pattern or a grid, where different bilayer compositions and/or different ligands are placed in the grid pattern on the substrate. Once the bilayer is formed on the substrate, the selected ligand in the form of a lipid-polymer-ligand conjugate or lipid-ligand conjugate, is inserted into the planar bilayer by contacting the surface or specific surface regions of the planar bilayer with the conjugate in the presence of microwave irradiation.

IV. EXAMPLES

The following examples further illustrate the invention described herein and are in no way intended to limit the scope of the invention.

Materials: The lipids distearoylphosphatidylethanolamine (DSPE), cholesterol, partially hydrogenated soy phosphatidylcholine (HSPC), and methoxy(polyethylene glycol)-distearoyl phosphatidylcholine (mPEG-DSPE) were obtained from Avanti Polar Lipids, Inc. (Alabaster, Ala.).

Example 1

Stability of Lipid Particles During Microwave Exposure

A. Liposome Preparation

Liposomes were prepared from partially hydrogenated soy phosphatidylcholine (HSPC), cholesterol, and methoxy (polyethylene glycol)-distearoylphosphatidyl-ethanolamine (mPEG-DSPE) (55:40:5 molar ratio) by lipid film hydration, followed by membrane extrusion (Gabizon, et al., J. Natl.

Cancer Inst., 81(19):1484 (1989)). The lipids were dissolved in a choloroform/methanol mixture in a round-bottomed flask. Using a rotary evaporatory, the solvent was removed to form a thin lipid film. Multilamellar liposomes were formed by vigorous shaking of the lipid film in an aqueous solution of 100 mM ammonium sulfate and 1 mM deferoxamine. Liposomes were subsequently extruded stepwise through polycarbonate membranes with gradually decreasing pore sizes from 0.2 to 0.05 µm using a high or medium pressure extruder. Vesicles having a particle size of between 70-100 nm were obtained, as determined by dynamic light scattering.

Unentrapped ammonium sulfate and deferoxamine were removed by filtration of the liposome suspension through chromatography columns. Doxorubicin was dissolved in saline (4 mg/mL) and mixed with the liposome suspension after filtration. The liposome-doxorubicin mixture was incubated for 1 hour at 60° C. Loading of doxorubicin into the liposome occurred as a result of the proton gradient created by the ammonium sulfate (Haran et al., Biochem. Biophys. Acta, 1151(2):201 (1993)). At the end of the incubation period, unentrapped doxorubicin was removed by passage of the liposome suspension through a cation-exchange resin.

B. Exposure to Microwave Irradiation

The liposomes were incubated for various times in a Spectra microwave oven (Model N KOR-802B, made in France) with an 850 W capacity, using a power level of 510 W (60% of total). Release of entrapped doxorubicin was determined to assess stability of the liposomes to microwave exposure. Specifically, the amount of doxorubicin released from the liposomes and the amount of liposomal doxorubicin were determined, respectively, in the presence and absence of Dowex 50×4-400 cation exchange resin (Aldrich Chemical Co., Inc. USA; Druckman et al., Biochem. Biophys. Acta, 980:381 (1989); Amselem et al., J. Pharm. Sci., 79:1045 (1990)). Liposome integrity was assessed from size measurements before and after incubation on a High Performance Particle Sizer ALV-NIBS/HPPS with ALV-5000/EPP multiply digital correlator (ALV-Laser Vertriebsgesellschaft GmbH, Langen, Germany). The results are shown in FIG. 1.

Example 2

Insertion of Lipid-Polymer-Ligand Conjugate into Pre-formed Liposomes

A. Conjugate Preparation

A lipid-polymer-ligand conjugate was prepared by reacting a single chain Fv (scFv) antibody fragment having binding affinity for c-erbB-2 receptor epitope (PCT/US99/07395, published as WO 99/55367) with a reactive PEG-DSPE conjugate, using previously described techniques (U.S. Pat. No. 6,180,134;

Zalipsky, S. et al., FEBS Lett, 353:71 (1994)). Briefly, distearolyphosphatidyl-ethanolamine (DSPE) and a heterobifunctional PEG derivative, N-hydroxy-succinimidyl-PEG-maleimide, are reacted to form a DSPE-PEG-maleimido conjugate. The malemido group at the free PEG end is reactive toward thiol moieties on the protein. The scFv antibody fragment is reacted with the DSPE-PEG-maleimido to form a DSPE-PEG-scFv conjugate.

B. Conjugate Insertion

Liposomes were prepared as described in Example 1A, but contained no doxorubicin. The pre-formed liposomes and a suspension of DSPE-PEG-scFv conjugate micelles were mixed in a plastic microtube (1.7 mL capacity for sample volumes of 100 µL, MCT-175-C, Axygen, USA; 15 mL capacity for all other sample volumes, Miniplast, Israel) at a ratio of 6 µg targeting ligand per µmole phospholipids, at a total phospholipids concentration of 47 mmole/mL. The samples were treated according to one of the following incubation conditions:

1. 60° C. for 60 minutes;
2. room temperature (approximately 25° C.) for 72 hours;
3. 37° C. for 72 hours;
4. room temperature (approximately 25° C.) or 37° C. in the presence of 0.1% or 0.5% ethanol for various times;
5. 10 minutes or 20 minutes in ultrasonic bath (Laboratory Supplies Co., Inc., model G112SPIT, 600 V, 80 KC, 5 AMP) at room temperature (approximately 25° C.);
6. 30 seconds, 45 seconds, 1 minute, 1.5 minutes, 3 minutes, and 10 minutes incubation in a Spectra microwave oven at 510 W, with sample volumes of 100 µL, 300 µL, 500 µL, and 1000 µL.

After incubation, the extent of insertion of the conjugate into the pre-formed liposomes was determined using SEC-HPLC (column: TSKG4000SWxl, 7.8 mm×30 cm, 8 µm; guard Column: TSKGELxl, 6 mm×4 cm; mobil phase: 0.1 M $NaH_2PO_4$ with 0.1% SDS in water; flow rate: 1.0 mL/min; wavelength: 215 nm; injection volume: 50 µL; run time: 20 min), with analysis for the amount of conjugate in the suspension medium (not inserted into the liposomes) and the total amount of targeting ligand recovered. The results are summarized in Table 1 and FIGS. 1A-1B.

Example 3

Insertion of Fluorescent Lipid-Polymer Conjugate into Liposomes

A. Preparation of Fluorescent Lipopolymer Probe: DSPE-HC-PEG

Figure 2B:
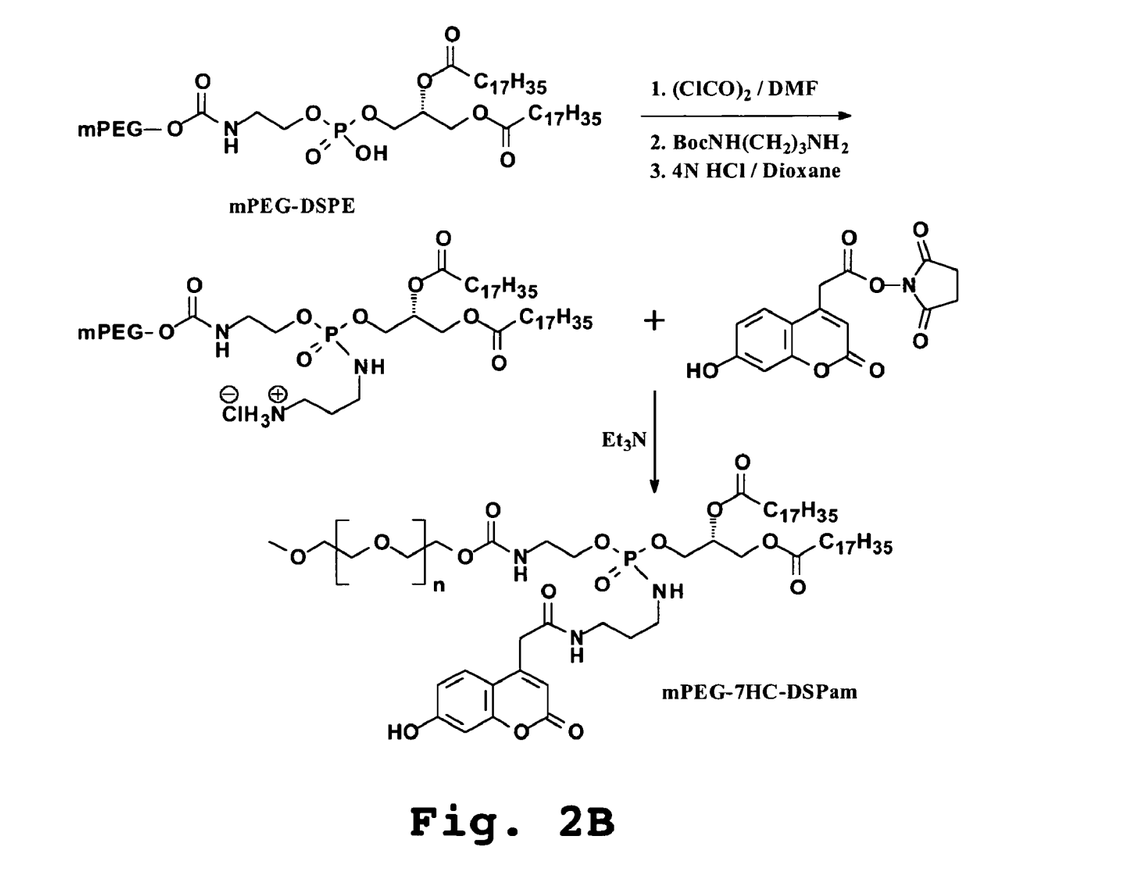
FIG. 2B shows the synthetic reaction scheme for preparation of the fluorescent lipopolymer of FIG. 2A.

The phosphoramide diester-linked conjugate of 7-hydroxycoumarin and mPEG-DSPE (FIG. 2A) was prepared according to the reaction scheme illustrated in FIG. 2B. mPEG-DSPE dissolved in dichloromethane was treated with oxalyl chloride and catalytic amount of DMF. The solution was evaporated to dryness and the residue redissolved in dichloromethane, cooled on ice and treated with triethylamine, 1-Boc-1,3-diaminopropane. After 15 min the reaction was complete. The solution was evaporated and the Boc-aminopropyl phosphoramidate product purified by silica gel chromatography (chloroform-methanol (95:5). Removal of the Boc group was effectd in 4M HCl in dioxane for one hour, and the aminopropyl functionalized mPEG-DSPE was treated with excess of succinimidyl ester of 7-hydroxycoumarinyl acetate in dichloromethane solution. After three hours the mPEG-7HC-DSPam product was purified by silica gel chromatography (chloroform-methanol, 95:5). Overall yield was approximately 50%. The material was characterized by NMR, MS and spectrofluorometry.

B. Insertion of Lipopolymer Probe into Liposomes

Liposomes, prepared as described in Example 1A, but containing no doxorubicin, were incubated with the fluorescent lipopolymer probe, DSPE-HC-PEG, for 15, 30, 45, or 60 seconds in a microwave oven according to the conditions set forth in Example 1. Fluorescence of each sample was measured using an LS550B luminescence spectrometer (Perkin Elmer, Norwalk, Conn.) after incubation, and each hour during a five hour period thereafter, and after 21 hours storage at room temperature (22° C.). The results are shown in FIG. 3.

Example 4

Insertion of Lipid-Polymer Conjugate into Phosphatidycholine Liposomes

Liposomes comprised of egg phosphatidylcholine (EPC) and labeled with a pH-sensitive probe, 7-heptadecyl-4-hydroxycoumarin ($C_{17}HC$) (FIG. 4A) or 1,2-dioleoyl-sn-glycero-3-phosphoethanolamine (DOPE-HC) (FIG. 4B), were prepared by thin film hydration followed by down sizing using extrusion. Briefly, EPC and one of the pH-sensitive probes were dissolved in an organic solvent in a round-bottomed flask. The solvent was removed by rotary evaporation to form a thin lipid film that was hydrated with an aqueous buffer to form multilamellar liposomes. The liposome suspension was sized by extrusion through polycarbonate membranes to an average diameter of 100 nm.

A conjugate of DSPE-PEG (PEG MW 2000 Daltons) was obtained commercially. A micellar suspension of the DSPE-PEG conjugate was mixed with a suspension of the labeled-EPC liposomes were incubated for 90 seconds in the presence of microwave irradiation in a conventional microwave oven operated at 60% power (Spectra, 850 W capacity). The extent of conjugate insertion was determined by the shift in the apparent pKa of HC moiety. The results are shown in Table 3.

With respect to the liposomes labeled with $C_{17}HC$, the apparent pKa of $C_{17}HC$ was calculated from the change of the ratio of excitation wavelengths 380/330 (emission wavelength 450 nm) as a function of bulk pH (Zuidam and Barenholz, *Biochim Biophys Acta*, 1329(2):211-22 (1997)). Fluorescence was measured using an LS-50B luminescence spectrometer (Perkin Elmer, Norwalk, Conn.). As a comparative reference, the insertion of DSPE-PEG into the same liposomes at room temperature was also measured. The results are shown in Table 4.

With respect to the liposomes labeled with DOPE-HC, the apparent pKa of DOPE-HC was calculated from the change of the ratio of excitation wavelengths 370/408 (emission wavelength 480 nm) as a function of bulk pH. Fluorescence was measured using an LS-50B luminescence spectrometer (Perkin Elmer, Norwalk, Conn.) immediately after exposure of microwave irradiation and 48 hours after exposure. The results are shown in Table 4.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method for inserting a lipid-linked moiety into a lipid assembly, comprising: contacting a lipid assembly comprising HSPC, cholesterol, EPC or mPEG-DSPE and a lipid-linked moiety comprising a DSPE-PEG conjugate in the presence of 510W of microwave energy for between 30 seconds and 10 minutes, thereby inserting the lipid linked moiety into a lipid assembly, wherein said lipid assembly is selected from the group consisting of a lipid monolayer, a lipid bilayer, a liposome, a micelle, or an emulsion envelope monolayer.

2. The method of claim 1, wherein said lipid assembly comprises an entrapped therapeutic agent.

* * * * *